(12) United States Patent
Rush et al.

(10) Patent No.: US 12,042,190 B2
(45) Date of Patent: Jul. 23, 2024

(54) BONE FRACTURE FIXATION DEVICE AND RELATED SYSTEMS AND METHODS

(71) Applicant: Surgical Design Innovations II, LLC, Johnston, IA (US)

(72) Inventors: Shannon M. Rush, San Jose, CA (US); David Kawalik, Chandler, AZ (US); Michael Lee, Johnston, IA (US); Jordan Grossman, Akron, OH (US); Troy J. Boffeli, Woodbury, MN (US); Mark Hardy, Lakewood, OH (US)

(73) Assignee: Surgical Design Innovations II, LLC, Johnston, IA (US)

( * ) Notice: Subject to any disclaimer, the term of this patent is extended or adjusted under 35 U.S.C. 154(b) by 0 days.

(21) Appl. No.: 17/859,529

(22) Filed: Jul. 7, 2022

(65) Prior Publication Data
US 2023/0008311 A1    Jan. 12, 2023

Related U.S. Application Data

(60) Provisional application No. 63/219,112, filed on Jul. 7, 2021.

(51) Int. Cl.
*A61B 17/72* (2006.01)
*A61B 17/88* (2006.01)
*A61B 17/68* (2006.01)

(52) U.S. Cl.
CPC ...... *A61B 17/7233* (2013.01); *A61B 17/8897* (2013.01); *A61B 2017/681* (2013.01)

(58) Field of Classification Search
CPC .......................................... A61B 17/72–7291
See application file for complete search history.

(56) References Cited

U.S. PATENT DOCUMENTS

| | | | |
|---|---|---|---|
| 5,116,378 A * | 5/1992 | Carbone | A61B 17/7258 623/23.26 |
| 5,993,448 A | 11/1999 | Remmler | |
| 7,703,727 B2 * | 4/2010 | Selness | A47B 91/028 248/188.2 |
| 10,492,839 B2 * | 12/2019 | Wodajo | A61B 17/7225 |
| 10,751,094 B2 * | 8/2020 | Green | A61B 17/7053 |
| 2008/0269751 A1 * | 10/2008 | Matityahu | A61B 17/7283 606/301 |
| 2009/0216232 A1 * | 8/2009 | Buford, III | A61B 17/7208 29/244 |
| 2011/0066152 A1 * | 3/2011 | Keller | A61B 17/725 606/62 |
| 2011/0282395 A1 * | 11/2011 | Beyar | A61B 17/7233 606/301 |

(Continued)

FOREIGN PATENT DOCUMENTS

WO    2019155160 A1    8/2019

*Primary Examiner* — Eduardo C Robert
*Assistant Examiner* — Steven J Cotroneo
(74) *Attorney, Agent, or Firm* — Fredrikson & Byron, P.A.

(57) ABSTRACT

The various embodiments disclosed herein relate to bone fixation devices, including intramedullary fixation or fusion devices. The various devices disclosed include an intermedullary rod or device having a proximal and a distal portion. The proximal and distal portions having articulated ends that are coupled to form a joint. The joint may be actuated to reduce a fracture and realign the bone after insertion of the device into the bone.

20 Claims, 9 Drawing Sheets

(56) References Cited

U.S. PATENT DOCUMENTS

| | | | |
|---|---|---|---|
| 2012/0065638 A1* | 3/2012 | Moore | A61B 17/7225 606/62 |
| 2013/0150971 A1* | 6/2013 | DeFalco | A61F 2/44 623/17.16 |
| 2013/0325006 A1* | 12/2013 | Michelinie | A61B 17/1725 606/62 |
| 2013/0325007 A1* | 12/2013 | Beyar | A61B 17/725 606/62 |
| 2013/0325076 A1* | 12/2013 | Palmer | A61B 17/8635 606/104 |
| 2019/0015138 A1* | 1/2019 | Schwardt | A61B 17/62 |

* cited by examiner

BONE FRACTURE FIXATION DEVICE AND RELATED SYSTEMS AND METHODS

CROSS-REFERENCE TO RELATED APPLICATION(S)

This application claims the benefit under 35 U.S.C. § 119(e) to U.S. Provisional Application 63/219,112, filed Jul. 7, 2021 and entitled "Bone Fracture Fixation Device and Related Systems and Methods," which is hereby incorporated herein by reference in its entirety.

FIELD

The various embodiments disclosed herein relate to bone fixation or fusion devices, including intramedullary fixation or fusion devices that are implanted into a target bone. In addition, other embodiments relate to systems and methods for implantation and adjustment of the bone fixation or fusion devices.

BACKGROUND

Bone fractures and dislocations, including fibular fractures and syndesmosis dislocations, are common injuries that currently require correction via known fracture/dislocation fixation devices and procedures. The known fracture and/or dislocation fixation devices and systems typically include a central nail and locking screws. Once the nail is implanted within the intramedullary canal of the target bone, there is little or no ability to adjust the nail or reduce the fracture. This lack of adjustability can result in poor reduction of the fracture, which can lead to poor or delayed healing and/or ankle misalignment.

There is a need in the art for improved intramedullary devices and systems for treatment of bone fractures and dislocations, including fibular fractures and syndesmosis dislocations.

BRIEF SUMMARY

Discussed herein are various bone fixation or fusion devices and related systems and methods.

In Example 1, a intramedullary fracture correction device comprises a first shaft, a second shaft operably coupled with the first shaft at a joint, and a drive mechanism disposed within the second shaft to actuate the joint to move the first and second shafts between an insertion position and an articulated position.

Example 2 relates to the fracture correction device according to Example 1, wherein the drive mechanism comprises a drive shaft operably coupled to a gear, wherein the gear is operably coupled to the first rod shaft.

Example 3 relates to the fracture correction device according to Example 2, wherein the first shaft comprises a first mateable coupling mechanism, wherein the gear is operably coupled to the first mateable coupling mechanism.

Example 4 relates to the fracture correction device according to Example 2, wherein the drive shaft comprises a mateable coupling feature disposed at a distal end of the drive shaft, wherein a driving tool can be coupled to the mateable coupling feature, whereby the driving tool can rotate the drive shaft.

Example 5 relates to the fracture correction device according to Example 1, wherein the first shaft further comprises a protrusion extending from a distal end of first shaft, wherein the first mateable coupling mechanism is disposed on the protrusion.

Example 6 relates to the fracture correction device according to Example 5, wherein the second shaft further comprises a channel defined in a proximal end of the second shaft, wherein the protrusion is slidably disposed within and attached to the channel.

In Example 7, a bone fixation device comprises a device body comprising a proximal segment and a distal segment. In addition, the device further comprises an adjustable joint formed between the proximal member and the distal member, wherein the proximal member and the distal member are movable substantially radially in relation to each other via the adjustable joint, and a drive mechanism operably coupled to the adjustable joint, wherein the drive mechanism is constructed and arranged to actuate the joint.

Example 8 relates to the bone fixation device according to Example 7, wherein the drive mechanism comprises a drive shaft and a gear operably coupled to the drive shaft.

Example 9 relates to the bone fixation device according to Example 8, wherein the gear is operably coupled to the proximal segment.

Example 10 relates to the bone fixation device according to Example 9, wherein the proximal segment comprises a first mateable coupling mechanism, wherein the gear is operably coupled to the first mateable coupling mechanism.

Example 11 relates to the bone fixation device according to Example 8, wherein the drive shaft comprises a driving tool coupling feature disposed at a distal end of the drive shaft, wherein a driving tool is coupleable to the driving tool mateable coupling feature, whereby the driving tool can rotate the drive shaft.

Example 12 relates to the bone fixation device according to Example 7, further comprising at least one aperture disposed within at least one of the proximal segment and the distal segment, wherein the at least one aperture is sized and shaped to receive an attachment screw.

Example 13 relates to the bone fixation device according to Example 7, wherein the distal segment comprises about a bend defined along a length of the distal segment.

In Example 14, a method for reducing a fracture comprises inserting a device into an intramedullary canal of a target bone, the device comprising a first shaft, a second shaft slidably coupled to the first shaft at a joint such that the first and second shafts can move in relation to each other along a path substantially transverse to a longitudinal axis of the first shaft, and a drive mechanism operably coupled to the joint. The method further comprises actuating the drive mechanism to cause the joint to reduce the fracture of the target bone.

Example 15 relates to the method according to Example 14, wherein the joint comprises a first mateable coupling mechanism disposed at a distal end of the first shaft.

Example 16 relates to the method according to Example 14, wherein the drive mechanism comprises an elongate drive shaft disposed within and extending along a length of the second shaft, the drive shaft comprising a driver tool attachment mechanism disposed at a distal end of the drive shaft, and a driven gear operably coupled to a proximal end of the elongate drive shaft, wherein the driven gear is operably coupled to the first mateable coupling mechanism.

Example 17 relates to the method according to Example 14, wherein the device further comprises at least one aperture within at least one of the first shaft and the second shaft.

Example 18 relates to the method according to Example 17, further comprising inserting at least one screw through the at least one aperture to secure the device to the target bone.

Example 19 relates to the method according to Example 14, wherein the target bone is a fibula.

Example 20 relates to the method according to Example 14, wherein the actuating the drive mechanism further comprises attaching a driver tool to the driver tool attachment mechanism and rotating the driver tool, whereby the first and second shafts move in relation to each other along the path substantially transverse to the longitudinal axis of the first shaft, wherein the path is an angled path.

While multiple embodiments are disclosed, still other embodiments of the disclosure will become apparent to those skilled in the art from the following detailed description, which shows and describes illustrative embodiments. As will be realized, the disclosure is capable of modifications in various obvious aspects, all without departing from the spirit and scope of the present disclosure. Accordingly, the drawings and detailed description are to be regarded as illustrative in nature and not restrictive.

DETAILED DESCRIPTION

The various embodiments disclosed and contemplated herein relate to adjustable intramedullary fixation and/or fusion devices and related systems and methods. Each of the devices is configured such that the device can be adjusted after implantation into the target bone. The devices disclosed and contemplated herein are taught with reference to the fibula but may be implemented in various other bones as would be appreciated by those of skill in the art. Certain implementations are designed specifically for fibular fractures and syndesmosis dislocations.

Figure 1A:
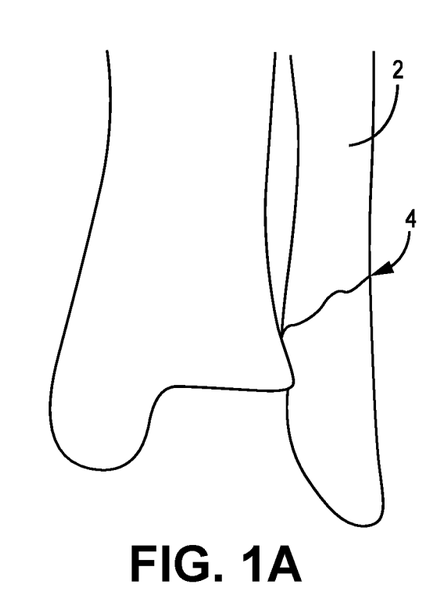
FIG. 1A is a schematic representation of a tibia and a fractured fibula.
Figure 1B:
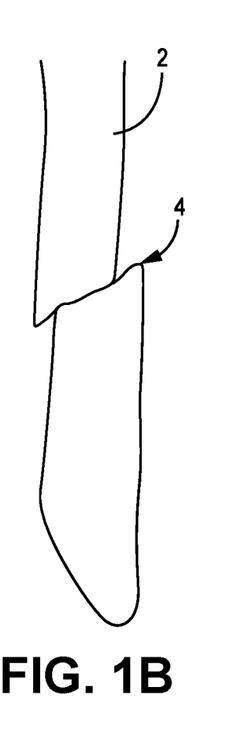
FIG. 1B is a schematic representation of a displaced fibular fracture.

As shown in FIGS. 1A and 1B, in one exemplary bone fracture that can be treated by the various embodiments herein, the fibula 2 may be fractured or dislocated, requiring surgical intervention to reduce and stabilize the injury. A fibular fracture 4 (or any target bone fracture) may be non-displaced (as shown in FIG. 1A) or displaced (as shown in FIG. 1B). A displaced fracture 4 must be reduced and realigned to allow for proper healing. Known fixation devices allow for little or no ability to adjust the placement of the fixation device and/or reduce the fracture 4 after insertion of the fixation device. In contrast, the various fixation device implementations disclosed and/or contemplated herein have an adjustable joint such that they allow for adjustments after insertion of the fixation device.

Figure 2:
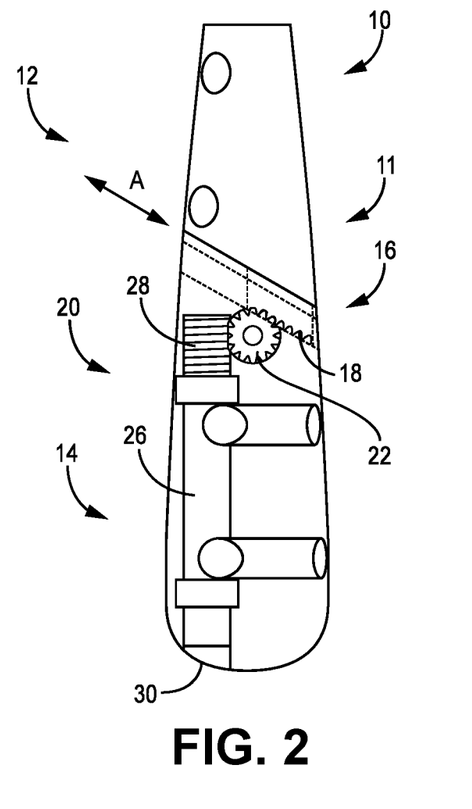
FIG. 2 is a side view of a fixation device, according to one implementation.
Figure 3:
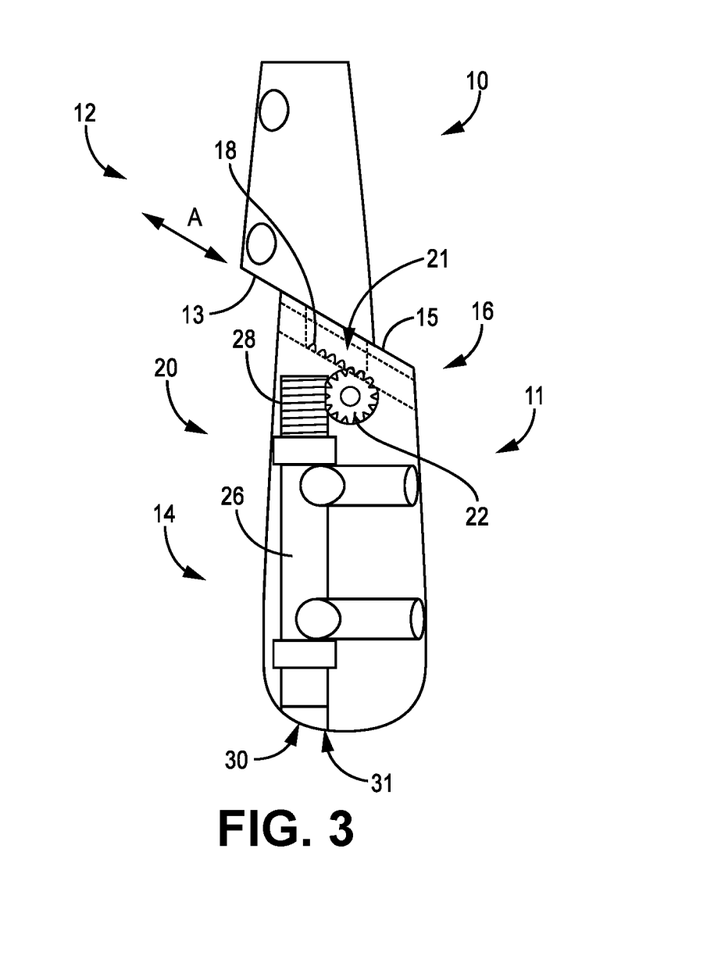
FIG. 3 is a further side view of the fixation device of FIG. 2 in the articulated position, according to one implementation.
Figure 4:
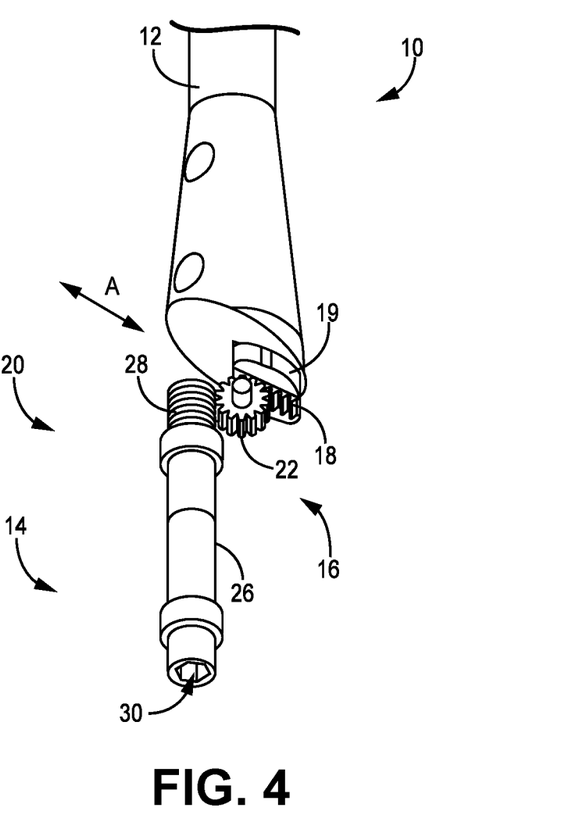
FIG. 4 is a bottom perspective view of a fixation device and drive mechanism with certain components removed for ease of viewing, according to one implementation.

As depicted in FIGS. 2-4 and 6A-7C, a fibular fixation device (also referred to herein as a "nail" or "rod") 10, according to one implementation, is an elongate device that is placed within the medullary canal of the fibula 2 or other target bone for fixation of the bone after an injury. The device 10 has device body 11 with a proximal elongate section 12 and a distal elongate section 14. The two portions 12, 14 of the body 11 are adjustably coupled to each other at a joint 16. FIG. 2 depicts the device body 11 in the aligned position (also referred to herein as an "insertion position"), while FIG. 3 shows the device body 11 in an articulated position, and FIG. 4 shows a close up view of the joint (also referred to as an "adjustment mechanism") 16.

The two sections 12, 14 of the body 11 are identified as the proximal section 12 and the distal section 14 based on the positioning of the body 11 within the target bone and thus the resulting position of each of the sections 12, 14. That is, upon insertion into the target bone (as will be discussed below in detail with respect to FIGS. 7A and 7B), the proximal section 12 will be disposed toward the proximal end of the bone, while the distal section 12 will be disposed toward the distal end of the bone.

Figure 7A:
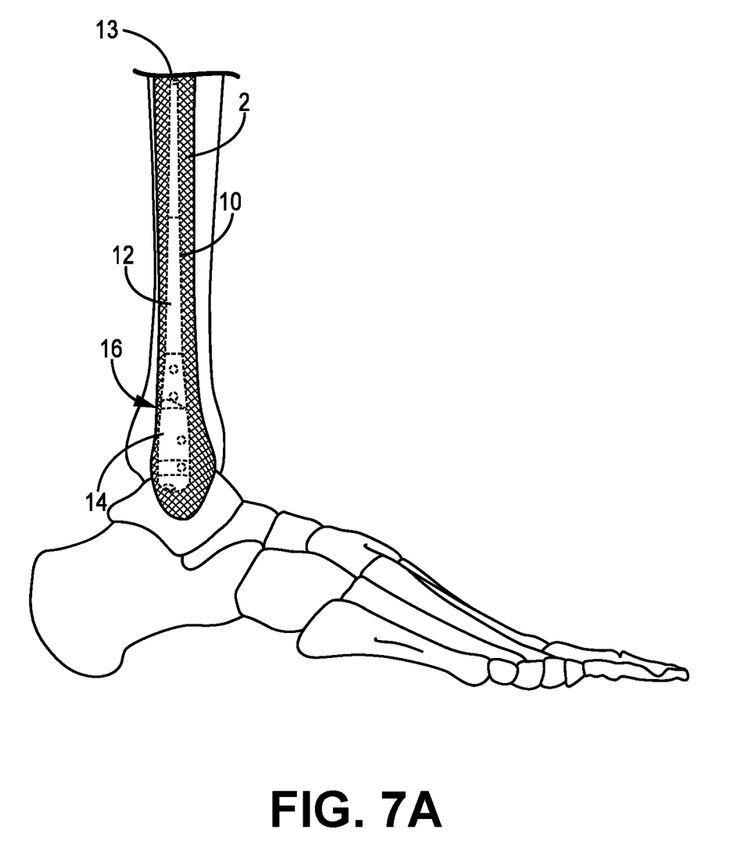
FIG. 7A is a lateral view of the fibula of a patient with an implanted fixation device, according to one implementation.
Figure 7B:
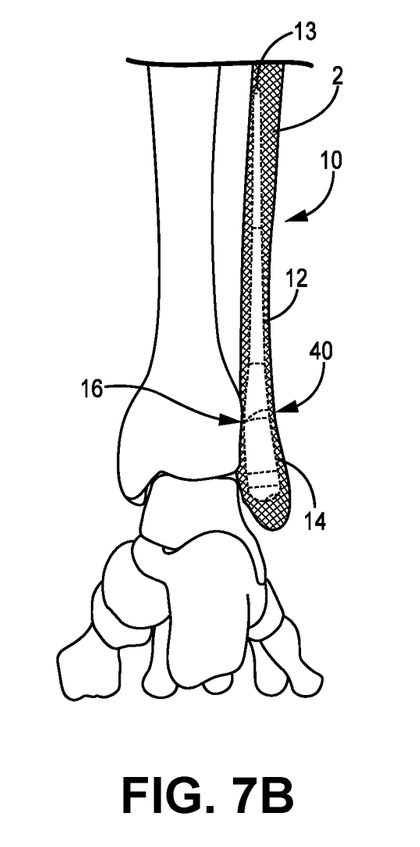
FIG. 7B is a posterior view of the fibula (and foot) of the patient of FIG. 7A with the implanted fixation device, according to one implementation.

As shown in FIGS. 7A and 7B, the proximal portion (also referred to as a "first shaft," "proximal member," "proximal shaft," "proximal pin," or "first rod") 12 of the device body 11 is an elongate structure having a blunted tip 13 at the proximal end for facilitating insertion into the medullary canal. As best shown in FIGS. 2-4, the distal end of the proximal shaft 12 forms a joint 16 with the proximal end of the distal shaft 14. The distal portion (also referred to as a "second shaft," "distal member," "distal shaft," "distal pin," or "second rod") 14 is coupled at its proximal end to the proximal portion 12 via the joint 16. The joint 16 is arranged such that the proximal portion 12 and distal portion 14 may move in relation to each other through the joint 16, in the direction of reference arrow A, which is substantially transverse to a longitudinal axis of the device body 11. That is, a drive mechanism 20 is provided that can actuate the two shafts 12, 14 to move substantially radially in relation to each other at the joint 16.

In the specific embodiment depicted herein, the joint 16 is configured as follows. The distal end of the proximal shaft 12 has a mateable mechanism or feature 18 disposed thereon that is mateably and moveably coupled with a driven gear (also referred to herein as a "cam drive" or "worm") 22 on the proximal end of the distal shaft 14 as shown. In one exemplary implementation as shown, the mateable mechanism 18 is a plurality of grooves 18 that can mateably couple with the threads or teeth of the driven gear 22 such that rotation of the gear 22 causes movement of the mateable mechanism 18 (and thus the proximal shaft 12). Alternatively, the mateable mechanism 18 can be any known structure, feature, or mechanism that can mateably couple with the driven gear in a similar fashion, including teeth, threads, etc. Further, the driven gear 22 can be any known type of gear, and thus can have any type of mateable structure that can mateably couple with the mateable mechanism or structure 18 such that rotation of the gear 22 can cause movement of the mechanism 18.

As best shown in FIG. 4, according to one specific implementation, the mateable mechanism or structure 18 is disposed or formed on a projection 19 that is disposed on the distal end of the proximal shaft 12. Alternatively, the mechanism 18 can be disposed or formed directly on the distal end of the proximal shaft 12. In addition, in certain embodiments including the device depicted in FIG. 4, the driven gear 22 is disposed at a position some distance distal from the proximal end of the distal shaft 14. That is, the proximal end of the distal shaft 14 has a channel 21 defined therein such that the threads or teeth of the gear 22 are disposed within the channel 21. In such implementations, the projection 19 of the proximal shaft is disposed within the channel 21 such that the mateable mechanism or structure 18 on the projection 19 is coupled with the teeth or threads of the gear 22. According to certain embodiments, the projection 19 has a coupling mechanism that slidably mates with and couples to a coupling mechanism associated with the channel 21, thereby ensuring that the two shafts 12, 14 remain coupled together while the drive mechanism 20 moves the two shafts 12, 14 in relation to each other as described herein.

The drive mechanism 20 disposed in the distal shaft 14 is made up of a drive shaft 26 and the rotatable driven gear 22, wherein the shaft 26 is rotatably coupled to the gear 22 at the mateable mechanism or structure 28 disposed at or near the proximal end of the shaft 26. In one embodiment, the mateable mechanism or structure 28 is a set of threads 28. Alternatively, any known mateable mechanism or structure that can mate with the gear 22 can be used. Thus, the gear 22 is operably coupled with both the mateable mechanism or structure 18 of the proximal portion 12 and the mateable mechanism or structure 28 of the drive shaft 26 such that rotation of the drive shaft 26 causes rotation of the mateable mechanism or structure 28, which thereby actuates the gear 22 to rotate on a different axis in comparison to the axis of the drive shaft 26. Actuation of the driven gear 22 causes the gear 22 to rotate, thereby mateably coupling with the mateable mechanism or structure 18 of the proximal portion 12 and urging the mateable mechanism or structure 18, and thus the proximal shaft 12, to move angularly relative to distal shaft 14 in the direction of reference arrow A.

As best shown in FIG. 3, according to certain implementations, regardless of the drive mechanism incorporated into the device 10, the distal end 13 of the proximal shaft 12 and the proximal end 15 of the distal shaft 14 are angled. That is, the two ends 13, 15 of the two shafts 12, 14 are each disposed at an angle as shown to create an angular movement when the drive mechanism 20 is actuated to move the two shafts 12, 14 in relation to each other. More specifically, the distal end 13 of the proximal shaft 12 is disposed at an angle in relation to the longitudinal axis of the shaft 12 that is not perpendicular to that axis. Similarly, the proximal end 15 of the distal shaft 14 is disposed at an angle that is parallel to and mateable with the angle of the distal end 13 of the proximal shaft 12 such that the two ends 13, 15 can be mateably coupled or disposed in moveable contact with each other as shown. Further, the threads 18 are disposed at the same angle or parallel to the angle of the two ends 13, 15. It is understood that the angular disposition of two ends 13, 15 as shown allows for both radial and axial movement of the two shafts 12, 14 in relation to each other. This angular movement both radially and axially can provide for adjustment of the fracture to align the two unaligned lengths of bone as desired.

In addition, the drive shaft 26 can extend to the distal end of the distal shaft 14 and have a connection component 30 at its distal end that is accessible via an opening 31 in the distal end of the distal shaft 14 such that a driver tool can be coupled to the connection component 30. The connection component 30 can be an opening, a protrusion, or any mateable connection mechanism 30 that allows for a driver tool to be coupled thereto. For example, the mateable connection mechanism 30 in this specific embodiment is an opening 30 defined in the distal end thereof whereby a mechanical actuation component (also referred to herein as a "driver component," "hex driver," or "driver") (not pictured) may be inserted into the opening 30 to rotate the drive shaft 26. More specifically, the opening 30 has a hexagonal shape (or any known mateable and actuable shape) that is mateable with the distal end of the driver (not shown) such that the driver can be used to rotate the shaft 26 via the hexagonally shaped opening 30. Alternatively, the distal end of the drive shaft 26 can have any known coupling mechanism or connection component that can mateably couple with an appropriate corresponding driver tool. The drive tool can used by a user (such as a surgeon) to actuate the drive mechanism 20 to adjust the joint 16. More specifically, rotation of the connection mechanism 30 (via a tool) causes rotation of the drive shaft 26, which causes rotation of the gear 22, thereby causing adjustment of the position of the proximal shaft 12 in relation to the distal shaft 14.

Figure 5A:
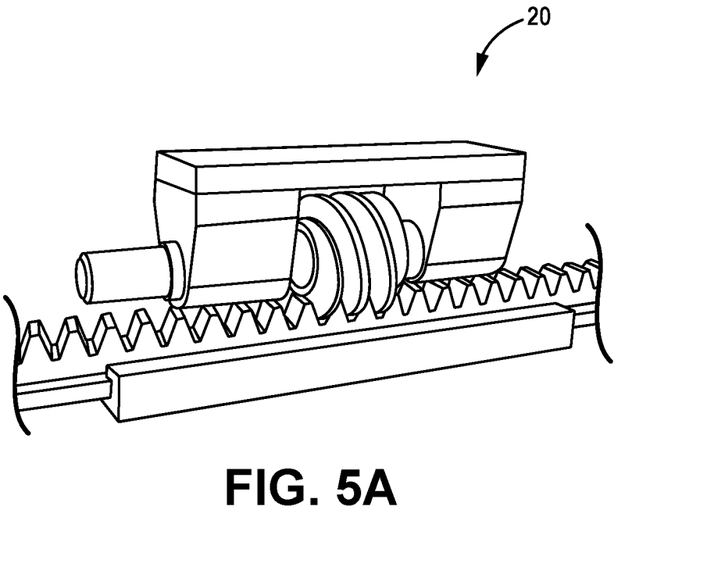
FIG. 5A depicts an exemplary rack and worm drive mechanism for incorporation into any of the embodiments herein, according to one embodiment.
Figure 5B:
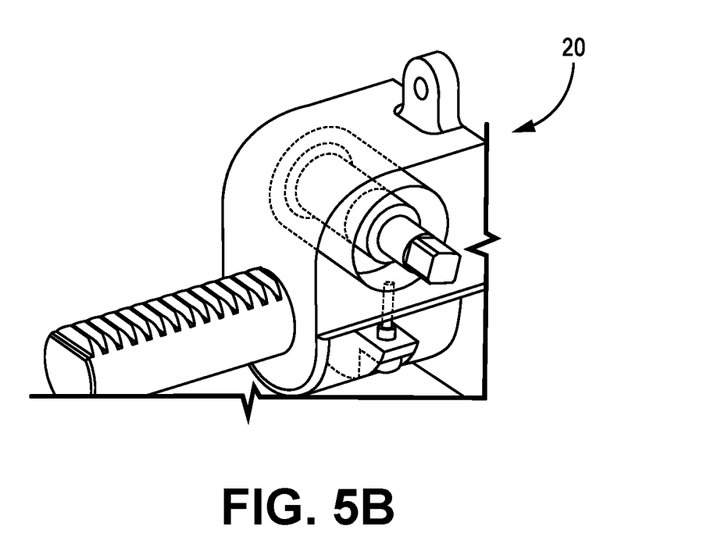
FIG. 5B depicts another exemplary rack and pinion drive mechanism for incorporation into any of the embodiments herein, according to a further embodiment.

It is understood that any other known drivers and similar mechanisms for use in medical devices can be used in place of the drive mechanism 20 as shown in FIGS. 2-4. For example, as depicted in FIGS. 5A and 5B, various other drive mechanisms 20 may be used in conjunction with the device 10. In one example, a rack and worm mechanism 20 as shown in FIG. 5A may be implemented. In another example, a rack and pinion or gear drive 20 as shown in FIG. 5B may be implemented.

Figure 6A:
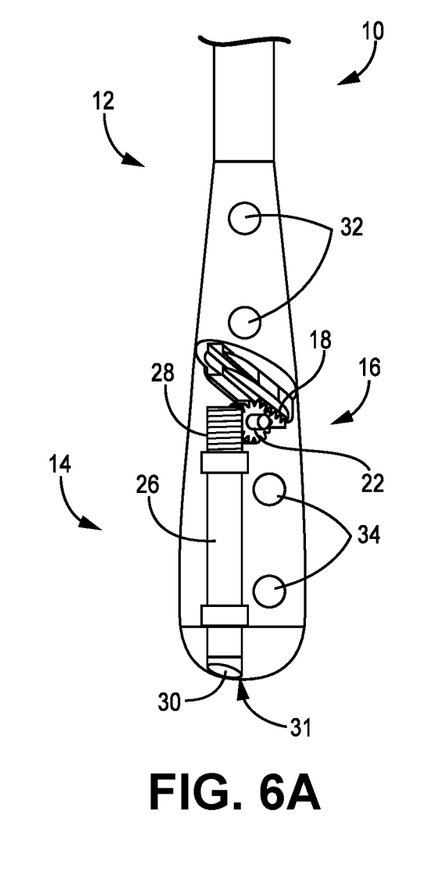
FIG. 6A is a side view of a fixation device, according to another implementation.
Figure 6B:
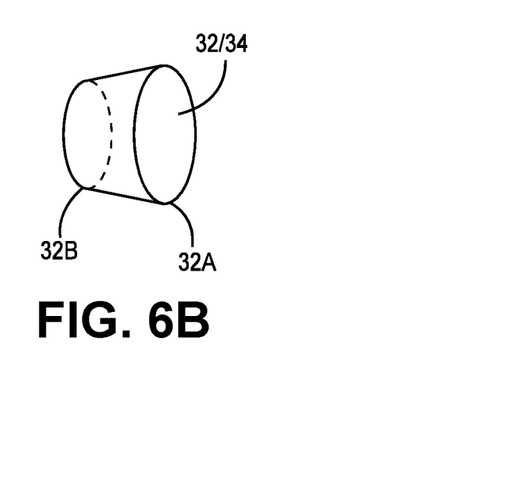
FIG. 6B is a side view of an exemplary aperture of the fixation device of FIG. 6A, according to one implementation.

As shown in 6A-6B, in certain implementations, the device 10 may also include one or more apertures 32, 34 for the insertion of locking screws, syndesmotic screws, or other similar, known fixation devices. The various screws or other types of known mechanisms may be disposed through the apertures 32, 34 within the device 10 to secure the device 10 in relation to the target bone of the patient and reduce instability. For example, proximal apertures 32 are disposed within the proximal shaft 12 and allow for angular placement of a syndesmotic screw or other screw across the syndesmosis and into the tibia. The distal apertures 34 are provided for fixation of the distal shaft 14 of the device 10 within the bone.

In some implementations, each of the apertures 32, 34 are arranged in the shape of a frustum, as best shown in the exemplary depiction of one such aperture 32, 34 in FIG. 6B. In these implementations, the medial portion of the aperture 32A is wider than the lateral portion of the aperture 32B. It is understood that various other configurations and shapes are possible.

In some implementations, the device 10 may be made of one or more metals. For example, the device 10 may be made of titanium, stainless steel, or other appropriate metal material or combination of metal materials as would be appreciated by those of skill in the art. Alternatively, the device 10 can be made of any known material for use in bone fixation and/or other medical devices.

It is understood that the device 10 may be of various sizes and shapes as necessary for the particular anatomy of the target bone, medullary canal, fracture, and patient. Various lengths and widths of the device 10 may be used.

Figure 7C:
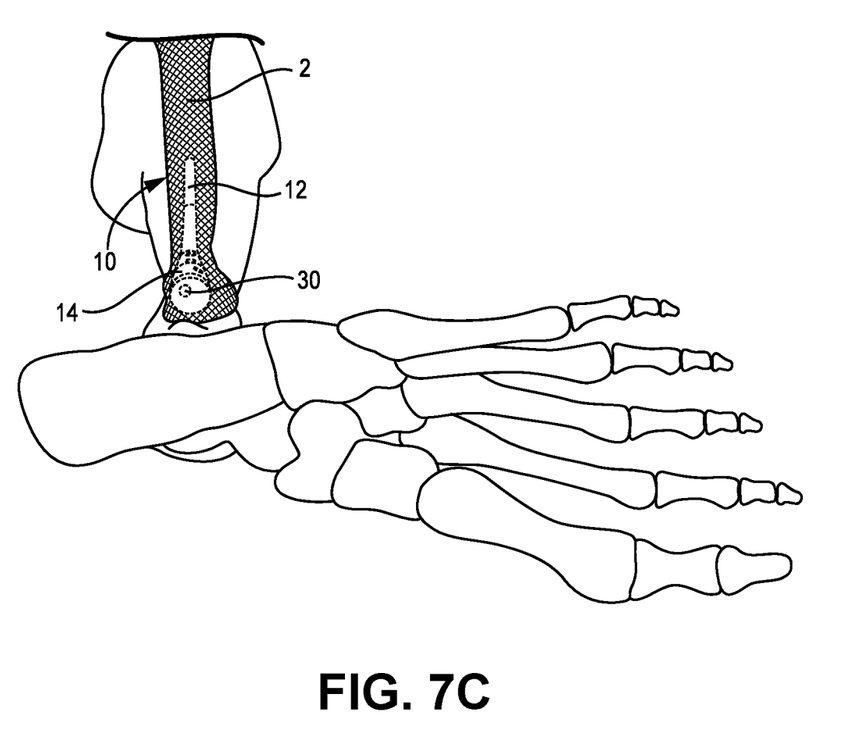
FIG. 7C is a bottom perspective view of the foot and fibula of the patient of FIG. 7A with the implanted fixation device, according to one implementation.

In use, as depicted in FIGS. 7A-7C, a fixation device 10—according to any embodiment disclosed or contemplated herein—may be placed within the medullary canal of the fibula 2 or other target bone via any appropriate surgical technique. For example, other target bones can include, but are not limited to, the humerus, tibia, femur, or any other long bone. In some implementations, the distal portion 14 has a bend (also referred to as "an angle" or "a curve") 40 as best shown in FIG. 7B that is intended to substantially replicate the bend or curve of the target fibula 2 and thereby ensure intramedullary placement. In various implementations, the bend 40 is about a 7° bend. Alternatively, depending on the target bone and any curvature thereof, any known angle that improves placement of the device 10 can be used. Of course, other shapes are possible.

In one example, the device 10 is inserted by drilling a pilot hole in the distal end of the fibula 2 of the patient. A guidewire may then be inserted into the medullary canal through the pilot hole and a hole drilled over the guidewire. The device 10 may be inserted within the hole within the medullary canal of the fibula 2. Of course, various other techniques and methods may be used, as would be appreciated by those of skill in the art.

An external targeting apparatus (not shown) may be used to assist in accurate and reproducible placement of the device 10 and/or screws. The external targeting apparatus may be disposed external to the fracture 4. It is understood that various targeting apparatuses are known in the art.

In various implementations, the device 10 should be placed within the fibula 2 or other target bone such that the joint 16 is substantially adjacent to the fracture 4. After the device 10 is placed within the fibula or other target bone, the drive mechanism 20 can be engaged to actuate the joint 16 to move the two shafts 12, 14 in relation to each other and thereby reduce the fracture 4 and realign the bone. The ability to actuate the proximal portion 12 relative to the distal portion 14 (and/or vice versa) after insertion allows a surgeon or other user to make corrections and adjustments to the bone alignment and fracture reduction after implantation of the device 10. The device 10 is placed within the bone and actuated such as to hold the bone in proper alignment during the healing process. Improved reduction of a fracture and proper bone alignment may lead to faster healing and better outcomes for patients.

Although the present disclosure describes various embodiments, persons skilled in the art will recognize that changes may be made in form and detail without departing from the spirit and scope of the various implementations herein.

What is claimed is:

1. An intramedullary fracture correction device comprising:
   (a) a first shaft comprising a first end;
   (b) a second shaft operably coupled with the first shaft at a joint, the second shaft comprising a second end disposed in slidable contact with the first end;
   (c) a channel defined in one of the first and second ends;
   (d) a protrusion extending from another of the first and second ends, wherein the protrusion is slidably disposed within and attached to the channel such that the first shaft is translatably attached to the second shaft at the first and second ends; and
   (e) a drive mechanism disposed within the second shaft, the drive mechanism comprising a drive shaft operably coupled to a gear, wherein the gear is operably coupled to the first shaft, wherein the drive mechanism is configured to actuate the protrusion and the channel to slide translationally in relation to each other such that the first and second shafts translate between an insertion position wherein the first and second shafts are coaxial and an articulated position wherein the first and second shafts are non-coaxial and substantially parallel.

2. The fracture correction device of claim 1, wherein the first shaft comprises a first mateable coupling mechanism, wherein the gear is operably coupled to the first mateable coupling mechanism.

3. The fracture correction device of claim 2, wherein the first mateable coupling mechanism is disposed on the protrusion.

4. The fracture correction device of claim 1, wherein the drive shaft comprises a mateable connection mechanism disposed at a distal end of the drive shaft, wherein a driving tool can be coupled to the mateable connection mechanism, whereby the driving tool can rotate the drive shaft.

5. The device of claim 1, wherein the first and second shafts are configured to simultaneously translate axially and radially in relation to each other between the insertion position and the articulated position.

6. A bone fixation device comprising:
   (a) a device body comprising:
      (i) a proximal segment comprising a first end; and
      (ii) a distal segment comprising a second end disposed in slidable contact with the first end;
   (b) an adjustable joint disposed at the first end and second ends, the adjustable joint comprising:
      (i) a channel defined in and extending radially across one of the first and second ends; and
      (ii) a protrusion extending from another of the first and second ends, wherein the protrusion is slidably disposed within and attached to the channel,
      wherein the proximal segment and the distal segment are movable via the adjustable joint between a first coaxial configuration and a second non-coaxial and substantially parallel configuration; and
   (c) a drive mechanism operably coupled to the adjustable joint, the drive mechanism comprising a drive shaft and a gear operably coupled to the drive shaft, wherein the drive mechanism is constructed and arranged to actuate the proximal segment and the distal segment to move between the first configuration and the second configuration via the adjustable joint.

7. The device of claim 6, wherein the gear is operably coupled to the protrusion.

8. The device of claim 7, wherein the protrusion comprises a first mateable coupling mechanism, wherein the gear is operably coupled to the first mateable coupling mechanism.

9. The device of claim 6, wherein the drive shaft comprises a driving tool connection mechanism disposed at a distal end of the drive shaft, wherein a driving tool is coupleable to the driving tool connection mechanism, whereby the driving tool can rotate the drive shaft.

10. The device of claim 6, further comprising at least one lumen extending radially through each of the proximal segment and the distal segment, wherein the at least one lumen is sized and shaped to receive an attachment screw.

11. The device of claim 6, wherein the distal segment comprises about a bend defined along a length of the distal segment.

12. The device of claim 6, wherein the proximal segment and the distal segment are simultaneously translatable both radially and axially in relation to each other.

13. A method for reducing a fracture, comprising:
inserting a device into an intramedullary canal of a target bone with a displaced fracture such that the target bone has a first bone portion and a second bone portion separated from the first bone portion at the displaced fracture, the device comprising:
  (a) a first shaft;
  (b) a second shaft slidably coupled to the first shaft at a joint such that the first and second shafts can move in relation to each other along a translational path; and
  (c) a drive mechanism operably coupled to the joint;
positioning the device such that the first shaft is disposed within the first bone portion, the second shaft is disposed within the second bone portion, and the joint is disposed at or near the displaced fracture;
attaching the first shaft to the first bone portion and the second shaft to the second bone portion; and
actuating the drive mechanism to urge the first and second shafts to simultaneously move along the translational path at the joint such that the first shaft and the first portion of the target bone move in a first biplanar direction and such that the second shaft and the second portion of the target bone move in a second, opposite biplanar direction, thereby lengthening the bone and reducing the fracture of the target bone.

14. The method of claim 13, wherein the joint comprises a first mateable coupling mechanism disposed at a distal end of the first shaft.

15. The method of claim 14, wherein the drive mechanism comprises:
  (a) an elongate drive shaft disposed within and extending along a length of the second shaft, the drive shaft comprising a driver tool attachment mechanism disposed at a distal end of the drive shaft; and
  (b) a driven gear operably coupled to a proximal end of the elongate drive shaft, wherein the driven gear is operably coupled to the first mateable coupling mechanism.

16. The method of claim 13, wherein the device further comprises at least one lumen within each of the first shaft and the second shaft.

17. The method of claim 16, wherein the attaching the first shaft to the first bone portion comprises inserting at least one first screw through the at least one lumen in the first shaft to secure the first shaft to the first bone portion and the attaching the second shaft to the second bone portion comprises inserting at least one second screw through the at least one lumen in the second shaft to secure the second shaft to the second bone portion.

18. The method of claim 13, wherein the target bone is a fibula.

19. The method of claim 13, wherein the actuating the drive mechanism further comprises attaching a driver tool to the driver tool attachment mechanism and rotating the driver tool, whereby the first and second shafts move in relation to each other along the path substantially transverse to the longitudinal axis of the first shaft, wherein the path is an angled path.

20. The method of claim 13, wherein the actuating the drive mechanism to urge the first and second shafts to simultaneously move along the translational path transposes a portion of the target bone in relation to another portion of the target bone.

* * * * *